(12) United States Patent
Foster et al.

(10) Patent No.: US 11,464,987 B2
(45) Date of Patent: Oct. 11, 2022

(54) IMPLANTABLE MEDICAL DEVICE AND DELIVERY CATHETER APPARATUS SYSTEM AND METHOD

(71) Applicant: Cardiac Pacemakers, Inc., St Paul, MN (US)

(72) Inventors: Arthur J. Foster, Blaine, MN (US); Benjamin J. Haasl, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 66 days.

(21) Appl. No.: 16/951,560

(22) Filed: Nov. 18, 2020

(65) Prior Publication Data
US 2022/0152405 A1    May 19, 2022

Related U.S. Application Data

(60) Provisional application No. 62/937,573, filed on Nov. 19, 2019.

(51) Int. Cl.
*A61N 1/375* (2006.01)
*A61N 1/05* (2006.01)

(52) U.S. Cl.
CPC ......... *A61N 1/37518* (2017.08); *A61N 1/057* (2013.01); *A61N 1/0558* (2013.01); *A61N 1/0573* (2013.01); *A61N 1/3752* (2013.01); *A61N 2001/058* (2013.01)

(58) Field of Classification Search
CPC .. A61N 1/37518; A61N 1/0558; A61N 1/057; A61N 1/0573; A61N 1/3752; A61N 2001/058
See application file for complete search history.

(56) References Cited

U.S. PATENT DOCUMENTS

| | | | | | |
|---|---|---|---|---|---|
| 4,672,979 | A | * | 6/1987 | Pohndorf | A61N 1/375 607/126 |
| 5,876,431 | A | * | 3/1999 | Spehr | A61N 1/057 607/126 |
| 6,947,782 | B2 | * | 9/2005 | Schulman | H01R 24/20 607/116 |
| 2003/0040787 | A1 | * | 2/2003 | Flynn | A61N 1/056 607/122 |
| 2009/0082828 | A1 | * | 3/2009 | Ostroff | A61N 1/37205 607/9 |
| 2011/0237967 | A1 | * | 9/2011 | Moore | A61N 1/3787 607/9 |
| 2016/0114157 | A1 | * | 4/2016 | Haasl | A61N 1/0587 607/119 |

* cited by examiner

*Primary Examiner* — Eugene T Wu
(74) *Attorney, Agent, or Firm* — Nelson Mullins Riley & Scarborough LLP (57) ABSTRACT

An implantable medical device includes a device housing, a fixation device, a first prong projecting from a proximal end of the device housing and a second prong projecting from the proximal end of the device housing. The second prong is spaced apart from the first prong. The first prong includes a first flange projecting away from a longitudinal axis of the device housing. The second prong includes a second flange projecting away from the longitudinal axis. The first prong and the second prong are configured to extend to a first flange diameter in a relaxed configuration and to extend to a second flange diameter in an expanded configuration.

19 Claims, 8 Drawing Sheets

IMPLANTABLE MEDICAL DEVICE AND DELIVERY CATHETER APPARATUS SYSTEM AND METHOD

CROSS REFERENCE TO RELATED APPLICATION

This application claims priority to Provisional Application No. 62/937,573, filed Nov. 19, 2019, which is herein incorporated by reference in its entirety.

TECHNICAL FIELD

The present disclosure relates to implantable medical devices. More specifically, the disclosure relates to medical devices and delivery systems for medical devices.

BACKGROUND

Implantable medical devices, such as medical electrical leads, must often be implanted with the aid of an introducer or delivery catheter. The delivery catheter positions the implantable medical device with the aid of a stylet extending through the coil conductor, or similar structure, within the implantable medical device. The implantable medical device is then fixated to tissue with a fixation element, such as a fixation helix, for example. Fixation is typically achieved by rotating the stylet or, in some cases, the coil conductor. The need for the implantable medical device to accommodate the stylet, which can have a diameter as small as 0.20 mm-0.43 mm", or a coil conductor to be large enough to transmit sufficient torque to activate the fixation element, limits how small the implantable medical device diameter can be. Thus, for example, medical electrical leads are limited to a diameter of from about 1.3 mm-2.0 mm at a minimum.

The human body responds more favorably to smaller implantable medical devices. Thus, there is a need for improvements in implantable medical devices and their delivery systems that allows for smaller implantable medical devices.

SUMMARY

Example 1 is an implantable medical device including a device housing, a fixation device, a first prong projecting from a proximal end of the device housing and a second prong projecting from the proximal end of the device housing. The second prong is spaced apart from the first prong. The first prong includes a first flange projecting away from a longitudinal axis of the device housing. The second prong includes a second flange projecting away from the longitudinal axis. The first prong and the second prong are configured to extend to a first flange diameter in a relaxed configuration and to extend to a second flange diameter in an expanded configuration.

Example 2 is the implantable medical device of Example 1, wherein the device is configured to couple to a delivery catheter when the first prong and the second prong are in the expanded configuration, and to decouple from the delivery catheter when the first prong and the second prong are in the relaxed configuration.

Example 3 is the implantable medical device of Example 1, further including an electrode and an electrical conductor. The electrical conductor includes a proximal end and a distal end. The distal end is electrically coupled to the electrode and the proximal end is configured to electrically couple to a medical electrical device.

Example 4 is the implantable medical device of Example 3, where in the fixation device is the electrode.

Example 5 is the implantable medical device of Example 3 or Example 4, wherein the implantable medical device is a first implantable medical device, and further including a second implantable medical device substantially similar to the first implantable medical device, the proximal end of the electrical conductor of the second implantable medical device electrically coupled to the first implantable medical device.

Example 6 is the implantable medical device of any of Examples 1-5, wherein the first prong further includes a first set of internal threads projecting toward the longitudinal axis and the second prong further includes a second set of internal threads projecting toward the longitudinal axis. The first set of threads and the second set of internal threads are configured to engage a delivery catheter in the expanded configuration and to disengage from the delivery catheter in the relaxed configuration.

Example 7 is an implantable medical device and delivery catheter apparatus system including the implantable medical device according to any of Examples 1-5 and a delivery catheter apparatus. The delivery catheter apparatus includes a delivery catheter, a driver coil and a driver wedge. The delivery catheter forms a catheter lumen extending from a proximal end of the delivery catheter to a distal end of the delivery catheter. The driver coil extends through the catheter lumen. The driver coil forms a driver coil lumen. The driver wedge is disposed at a distal end of the driver coil. The driver wedge is configured to selectively engage the first prong and the second prong to place the first prong and the second prong in the expanded configuration, coupling the device to the delivery catheter, and to disengage from the first prong and the second prong to allow the first prong and the second prong to return to the relaxed configuration, decoupling the device from the delivery catheter.

Example 8 is the system of Example 7, wherein the catheter lumen includes a first lumen diameter at the distal end of the delivery catheter, a second lumen diameter proximal of the first lumen diameter and a third lumen diameter proximal of the second lumen diameter. The first lumen diameter is greater than the first flange diameter and less than the second flange diameter. The second lumen diameter is greater than or equal to the second flange diameter. The third lumen diameter is less than the second flange diameter.

Example 9 is the system of either of Examples 7 or 8, wherein the first prong further includes a first set of internal threads projecting toward the longitudinal axis and the second prong further includes a second set of internal threads projecting toward the longitudinal axis, and the driver wedge further includes a set of external threads configured to selectively engage the first set of internal threads and the second set of internal threads to place the first prong and the second prong in the expanded configuration and to disengage the first set of internal threads and the second set of internal threads to allow the first prong and the second prong to return to the relaxed configuration.

Example 10 is the system of any of Examples 7-9, wherein the driver wedge forms a driver wedge lumen extending through the driver wedge.

Example 11 is the system of Example 10, wherein the delivery catheter apparatus further includes a stylet configured to extend through the driver coil lumen and the driver wedge lumen and engage the fixation device to extend the fixation device from the distal end of the device housing.

Example 12 is the system of any of Examples 7-11, wherein the delivery catheter includes a cone projecting distally and radially outward from the distal end of the delivery catheter.

Example 13 is a method of decoupling a delivery catheter apparatus from an implantable medical device, the implantable medical device including a first prong including a first flange and a second prong including a second flange, the first flange and the second flange engaging an annular recess in a delivery catheter of the delivery catheter apparatus to couple the implantable medical device to the delivery catheter apparatus. The method includes rotating a driver wedge to disengage the driver wedge from the first prong and the second prong; removing the disengaged driver wedge from between the first prong and the second prong to release a compressive force exerted by the first prong and the second prong on the driver wedge, the released compressive force moving the first prong and the second prong toward each other, disengaging the first flange and the second flange from the annular recess; and retracting the delivery catheter proximally to uncouple the delivery catheter apparatus from the implantable medical device.

Example 14 is the method of Example 13, wherein rotating the driver wedge includes rotating a driver coil coupled to the driver wedge.

Example 15 is the method of either of Examples 13 or 14, wherein the implantable medical device is a medical electrical lead.

Example 16 is an implantable medical device including a device housing, a fixation device configured to extend from a distal end of the device housing, a first prong projecting from a proximal end of the device housing and a second prong projecting from the proximal end of the device housing. The second prong is spaced apart from the first prong. The first prong includes a first flange projecting away from a longitudinal axis of the device housing. The second prong includes a second flange projecting away from the longitudinal axis. The first prong and the second prong are configured to extend to a first flange diameter in a relaxed configuration and to extend to a second flange diameter in an expanded configuration.

Example 17 is the implantable medical device of Example 16, wherein the device is configured to couple to a delivery catheter when the first prong and the second prong are in the expanded configuration, and to decouple from the delivery catheter when the first prong and the second prong are in the relaxed configuration.

Example 18 is the implantable medical device of Example 16, where in the fixation device is a fixation helix.

Example 19 is the implantable medical device of Example 16, further including an electrode and an electrical conductor including a proximal end and a distal end, the distal end electrically coupled to the electrode and the proximal end configured to electrically couple to a medical electrical device.

Example 20 is the implantable medical device of Example 19, where in the fixation device is the electrode.

Example 21 is the implantable medical device of Example 19 or Example 20, wherein the implantable medical device is a first implantable medical device, further including a second implantable medical device substantially similar to the first implantable medical device, the proximal end of the electrical conductor of the second implantable medical device electrically coupled to the first implantable medical device.

Example 22 is the implantable medical device of any of Examples 17-21, wherein the first prong further includes a first set of internal threads projecting toward the longitudinal axis and the second prong further includes a second set of internal threads projecting toward the longitudinal axis. The first set of thread and the second set of internal threads are configured to engage the delivery catheter in the expanded configuration and to disengage from the delivery catheter in the expanded configuration.

Example 23 is an implantable medical device and delivery catheter apparatus system including an implantable medical device and a delivery catheter apparatus. The implantable medical device includes a device housing, a fixation device configured to extend from a distal end of the device housing, a first prong projecting from a proximal end of the device housing and a second prong projecting from the proximal end of the device housing. The second prong is spaced apart from the first prong. The first prong includes a first flange projecting away from a longitudinal axis of the device housing. The second prong includes a second flange projecting away from the longitudinal axis. The first prong and the second prong are configured to extend to a first flange diameter in a relaxed configuration and to extend to a second flange diameter in an expanded configuration. The delivery catheter apparatus includes a delivery catheter, a driver coil and a driver wedge. The delivery catheter forms a catheter lumen extending from a proximal end of the delivery catheter to a distal end of the delivery catheter. The driver coil extends through the catheter lumen. The driver coil forms a driver coil lumen. The driver wedge is disposed at a distal end of the driver coil. The driver wedge is configured to selectively engage the first prong and the second prong to place the first prong and the second prong in the expanded configuration to couple the device to the delivery catheter, and disengage from the first prong and the second prong to allow the first prong and the second prong to return to the relaxed configuration to decouple the device from the delivery catheter.

Example 24 is the system of Example 23, wherein the implantable medical device further includes an electrode and an electrical conductor. A distal end of the conductor is electrically coupled to the electrode and a proximal end of the conductor is configured to electrically couple to a medical electrical device.

Example 25 is the system of Example 24, where in the fixation device is the electrode.

Example 26 is the system of Example 24 or Example 25, wherein the implantable medical device is a first implantable medical device and delivery catheter apparatus is a first delivery catheter apparatus. The system further includes a second implantable medical device substantially similar to the first implantable medical device and a second delivery catheter apparatus substantially similar to the first delivery catheter apparatus. The proximal end of the electrical conductor of the second implantable medical device is electrically coupled to the first implantable medical device.

Example 27 is the system of any of Examples 23-26, wherein the catheter lumen includes a first lumen diameter at the distal end of the delivery catheter, a second lumen diameter proximal of the first lumen diameter and a third lumen diameter proximal of the second lumen diameter. The first lumen diameter is greater than the first flange diameter and less than the second flange diameter. The second lumen diameter is greater than or equal to the second flange diameter. The third lumen diameter is less than the second flange diameter.

Example 28 is the system of Example 27, wherein the second lumen diameter forms an annular recess, the first flange and the second flange are disposed at least partially within the annular recess in the expanded configuration and are not disposed within the annular recess in the relaxed configuration.

Example 29 is the system of any of Examples 23-28, wherein the first prong further includes a first set of internal threads projecting toward the longitudinal axis and the second prong further includes a second set of internal threads projecting toward the longitudinal axis. The driver wedge further includes a set of external threads configured to selectively engage the first set of internal threads and the second set of internal threads to place the first prong and the second prong in the expanded configuration and to disengage the first set of internal threads and the second set of internal to allow the first prong and the second prong to return to the relaxed configuration.

Example 30 is the system of Examples 23-29, wherein the driver wedge forms a driver wedge lumen extending through the driver wedge.

Example 31 is the system of Example 30, wherein the delivery catheter apparatus further includes a stylet configured to extend through the driver coil lumen and the driver wedge lumen and engage the fixation device to extend the fixation device from the distal end of the device housing.

Example 32 is the system of any of Examples 23-31, wherein the delivery catheter includes a cone projecting distally and radially outward from the distal end of the delivery catheter.

Example 33 is a method of decoupling a delivery catheter apparatus from an implantable medical device, the implantable medical device including a first prong including a first flange and a second prong including a second flange, the first flange and the second flange engaging an annular recess in a delivery catheter of the delivery catheter apparatus to couple the implantable medical device to the delivery catheter apparatus. The method includes rotating a driver wedge to disengage the driver wedge from the first prong and the second prong; removing the disengaged driver wedge from between the first prong and the second prong to release a compressive force exerted by the first prong and the second prong on the driver wedge, the released compressive force moving the first prong and the second prong toward each other, disengaging the first flange and the second flange from the annular recess; and retracting the delivery catheter proximally to uncouple the delivery catheter apparatus from the implantable medical device.

Example 34 is the method of Example 33, wherein rotating the driver wedge includes rotating a driver coil coupled to the driver wedge.

Example 35 is the method of Example 33 or Example 34, wherein the implantable medical device is a medical electrical lead.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

DETAILED DESCRIPTION

A more complete understanding is available by reference to the following detailed description of numerous aspects and embodiments of the disclosure. The detailed description which follows is intended to illustrate but not limit the disclosure.

In accordance with various aspects of the disclosure, an implantable medical device is understood to be completely introduced, surgically or medically, into the human body or by medical intervention into a natural orifice, and which is intended to remain after, at least temporarily, after the procedure. It is understood that the various embodiments can be implemented in any suitable medical device implanted in a patient by a delivery catheter and held in place, by a fixation mechanism. It is further understood that in embodiments can include tissue anchors, medical electrical leads, or other such devices. In embodiments in which embodiments include medical electrical leads, it is understood that such leads may be electrically coupled to medical electrical devices, such as, and without limitation, cardiac rhythm management (CRM) systems (e.g., a cardioverter-defibrillator (ICD) system, a pacemaker system, or a cardiac resynchronization system), implantable cardiac monitors, neurostimulation systems (e.g., a spinal cord stimulation system, a deep brain stimulation system, an overactive bladder system, a hypoglossal nerve stimulation system, or a vagus nerve stimulation system), implantable incontinence systems and implantable erectile dysfunction systems, for example.

Embodiments of the disclosure separates the need for some implantable medical device elements, such as coil conductors or retrieval tethers, for example, to serve as a portion of the delivery system or to activate a fixation element. The separation permits the medical device element, such as a coil conductor to be much smaller, as it need not accommodate a stylet or supply torque to activate a fixation element. The separation also allows for significant design flexibility in the position and orientation of the implantable medical device element.

Figure 1:
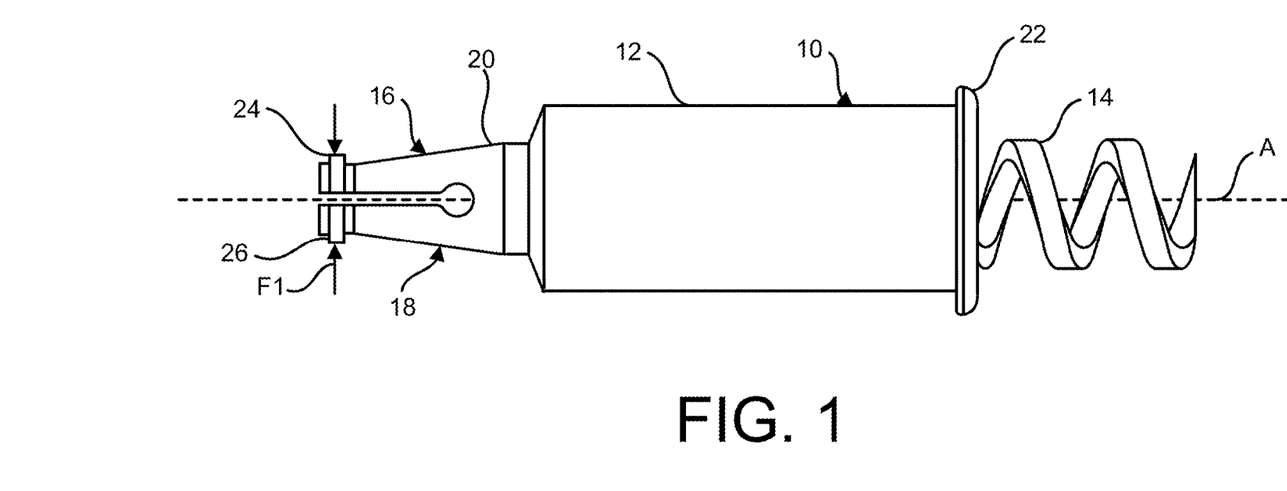
FIG. 1 is a side view of an implantable medical device, according to some embodiments of the disclosure.

FIG. 1 is a side view of an implantable medical device 10, according to some embodiments of the disclosure. As shown in FIG. 1, the implantable medical device 10 includes a device housing 12, a fixation device 14, a first prong 16, and a second prong 18. In some embodiments, the device housing 12 can be formed from a biocompatible non-conductive polymer such as, for example, an aromatic polyether-based thermoplastic polyurethane, polyether ether ketone, a polycarbonate based polyurethane, silicone rubbers, or a hybrid material composed of silicones and polyurethanes, for example.

The fixation device 14 is illustrated as a fixation helix. The fixation device 14 can be formed of any biocompatible material, such as platinum, platinum alloys, palladium, palladium alloys, titanium, cobalt-chromium-nickel alloys, nickel-cobalt-chromium-molybdenum alloys or stainless steel, for example. The fixation device 14 may be conductive, or non-conductive, depending the function of the implantable medical device 10. The fixation device 14 can be deployed by rotating a threaded structure (not shown) within the device housing 12. Although the fixation device 14 is illustrated as a fixation helix, it is understood that embodiments include other fixation devices, such as tines, for example.

In some embodiments, the first prong 16 and the second prong 18 are integrally formed with the device housing 12 and thus be composed of the same material as the device housing 12. In some other embodiments, the first prong 16 and the second prong 18 are formed of a different material coupled to the device housing 12. In some embodiments, the first prong 16 and the second prong 18 can be joined to the device housing 12 by laser welding, radio-frequency bonding, adhesive bonding or solvent bonding, for example.

As shown in FIG. 1, the device housing 12 has a proximal end 20 end and a distal end 22 opposite the proximal end 20. The device housing 12 also has a longitudinal axis A extending between the proximal end 20 and the distal end 22. The fixation device 14 is disposed at the distal end 22. The first prong 16 and the second prong 18 each project from the proximal end 20. The first prong 16 includes a first flange 24. The first flange 24 is spaced apart from the device housing 12 and projects away from the longitudinal axis A. Similarly, the second prong 18 includes a second flange 26. The second flange 26 is spaced apart from the device housing 12 and projects away from the longitudinal axis A.

In FIG. 1, the first prong 16 and second prong 18 are shown in a relaxed configuration. That is, there the first prong 16 and second prong 18 are in a neutral state, not subject to any forces that would cause the first prong 16 or second prong 18 to flex. Together, the first flange 24 and the second flange 26 extend to a first flange diameter F1 in the relaxed configuration.

The implantable medical device 10 can be quite small. In some embodiments, a diameter of the implantable medical device 10 can be as small as 1.5 mm, 1.6 mm, 1.7 mm, 1.8 mm, 1.9 mm or 2.0 mm, or as large as 2.2 mm, 2.4 mm, 2.6 mm, 2.8 mm or 3.0 mm, or may be within any range defined between any two of the foregoing values, such as 1.5 mm to 3.0 mm, 1.6 mm to 2.8 mm, 1.7 mm to 2.6 mm, 1.8 mm to 2.4 mm, 1.9 mm to 2.2 mm, 2.0 mm to 2.2 mm, 1.8 mm to 2.0 mm, or 1.7 mm to 2.0 mm, for example.

Figure 2:
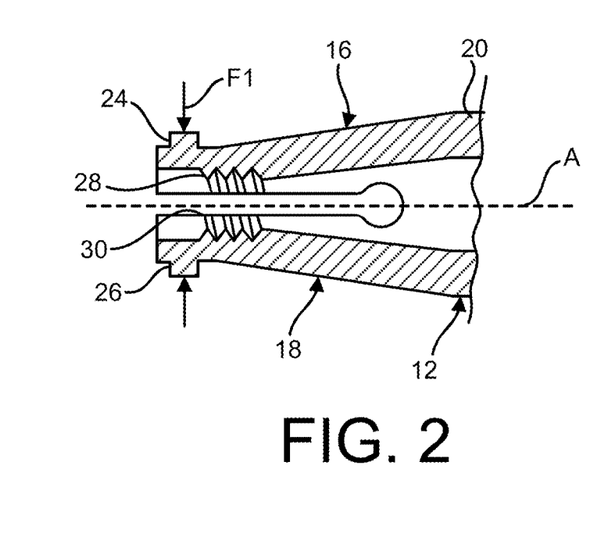
FIG. 2 is a side cross-sectional view of a portion of the implantable medical device of FIG. 1, according to some embodiments of the disclosure.

FIG. 2 is a side cross-sectional view of a portion of the implantable medical device 10 of FIG. 1, according to some embodiments of the disclosure. FIG. 2 shows that the first prong 16 further includes a first set of internal threads 28 and the second prong 18 further includes a second set of internal threads 30. The first set of internal threads 28 and the second set of internal threads 30 each project toward the longitudinal axis A. Together, the first set of internal threads 28 and the second set of internal threads 30 are disposed to provide a single threaded connection.

Although the embodiment of FIGS. 1 and 2 is shown with two prongs projecting from the proximal end 20 of the device housing 12, it is understood that embodiments include more than two prongs, such as three prongs, four prongs, or even more prongs, so long that the flanges projecting from the prongs extend to the first flange diameter F1 and that the internal threads projecting from the prongs are disposed to provide a single threaded connection.

Figure 3:
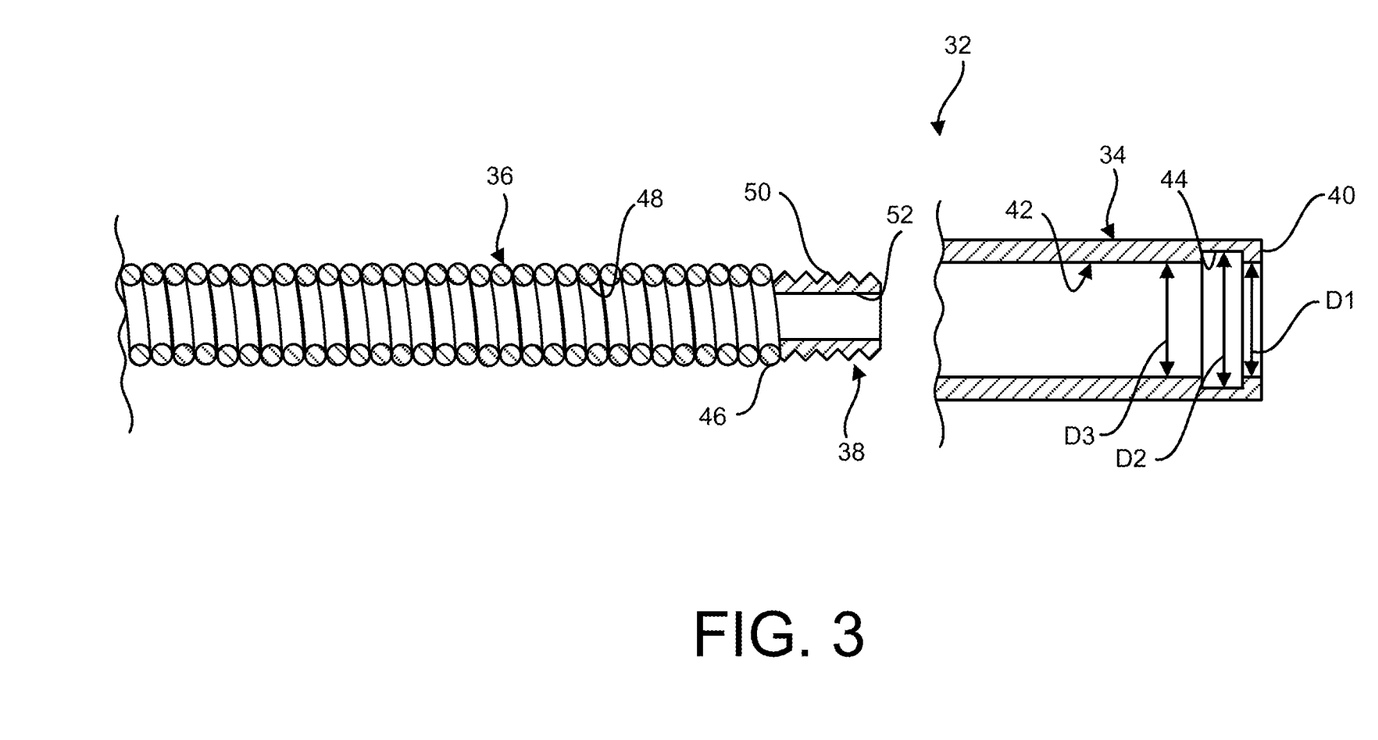
FIG. 3 is a side cross-sectional view of a delivery catheter apparatus, according to some embodiments of the disclosure.

FIG. 3 is a side cross-sectional view of portion of a delivery catheter apparatus 32, according to some embodiments of the disclosure. As shown in FIG. 3, the delivery catheter apparatus 32 includes a delivery catheter 34, a driver coil 36 and a driver wedge 38. For clarity and understanding, only a portion of the length of the delivery catheter 34 and of the driver coil 36 are shown. The delivery catheter 34 includes a distal end 40 and a proximal end (not shown) configured to extend outside of the patient when in use. The delivery catheter 34 is a tubular structure forming a catheter lumen 42 which extends from the distal end 40 to the proximal end (not shown). The catheter lumen 42 includes a first lumen diameter D1, a second lumen diameter D2 and a third lumen diameter D3. The first lumen diameter D1 is disposed at the distal end 40. The second lumen diameter D2 is disposed proximal of the first lumen diameter D1. The third lumen diameter D3 is disposed proximal of the second lumen diameter D2. Together, the first lumen diameter D1, the second lumen diameter D2 and the third lumen diameter D3 for an annular recess 44. In some embodiments, the third lumen diameter D3 may extend from the second lumen diameter D2 to the proximal end (not shown) of the delivery catheter 34. The delivery catheter 34 may be formed of a flexible, biocompatible polymer such as polyether polyurethanes, silicones, polyurethane silicone blends and polyesters, fore example.

The driver coil 36 includes a distal end 46 and a proximal end (not shown) configured to extend outside the patient when in use. The driver coil 36 forms a driver coil lumen 48 which extends from the distal end 46 to the proximal end (not shown). The driver coil 36 can be formed of platinum, palladium, titanium, cobalt-chromium-nickel alloys, nickel-cobalt-chromium-molybdenum alloys, nickel-titanium alloys, stainless steel or tantalum, for example.

As shown in FIG. 3, the driver wedge 38 is disposed at the distal end 46 of the driver coil 36. The driver wedge 38 includes a set of external threads 50. The driver wedge 38 forms a diver wedge lumen 52 extending through the driver wedge 38 as shown in FIG. 2. The driver wedge 38 can be formed of any biocompatible, rigid material, such as polyether ether ketone, platinum, palladium, titanium, cobalt-chromium-nickel alloys, nickel-cobalt-chromiummolybdenum alloys, nickel-titanium alloys, stainless steel or tantalum, for example. The driver wedge 38 can be coupled to the distal end 46 of the driver coil 36 by methods know in the art, such as welding, swaging, or an adhesive, for example. Alternatively, the driver wedge 38 can be formed of swaged and/or welded portions of the driver coil 36.

The driver coil 36 and driver wedge 38 are configured to be disposed within the catheter lumen 42 to guide the delivery catheter 34 and to selectively couple and decouple the delivery catheter apparatus 32 from the implantable medical device 10, as described below. The catheter lumen 42 is sized to accommodate the driver coil 36 and driver wedge 38 so that they can move along the delivery catheter 34.

Figure 4:
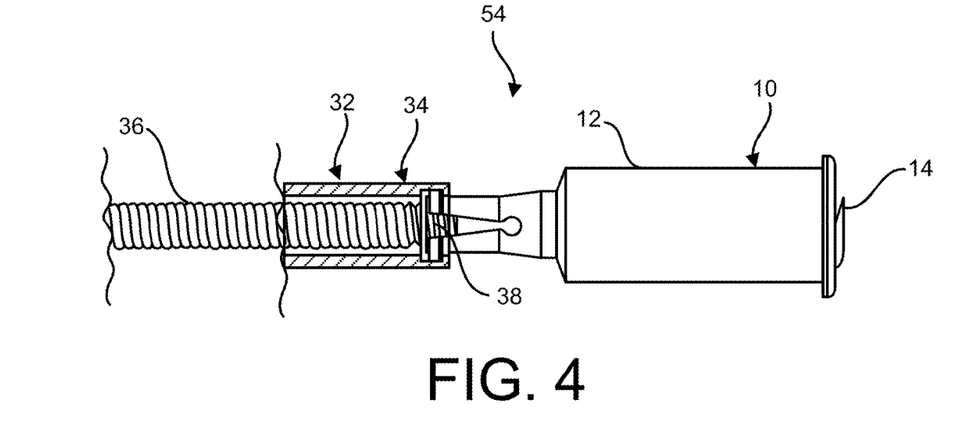
FIG. 4 is a side view of an implantable medical device and delivery catheter apparatus system, according to some embodiments of the disclosure.

FIG. 4 is a side view of an implantable medical device and delivery catheter apparatus system 54, according to some embodiments of the disclosure. The implantable medical device and delivery catheter apparatus system 54 includes the implantable medical device 10 and the delivery catheter apparatus 32, as described above. In FIG. 4, the implantable medical device 10 is coupled to the delivery catheter apparatus 32. So configured, the implantable medical device and delivery catheter apparatus system 54 can deliver the implantable medical device 10 to a site within a patient's body.

Figure 5:
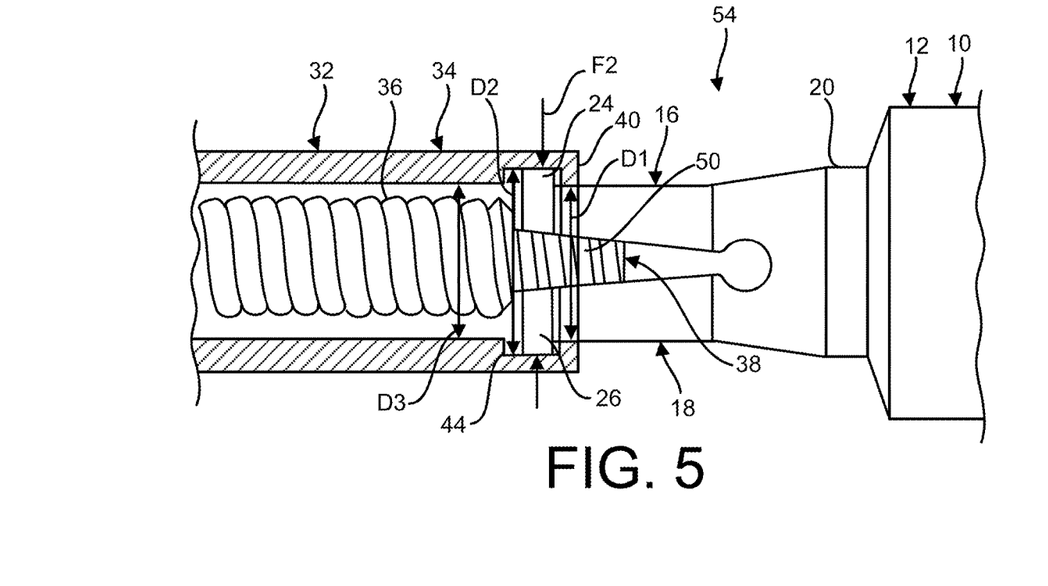
FIG. 5 is an enlarged side view of the portion of the implantable medical device and delivery catheter apparatus system of FIG. 4, where the implantable medical device couples to the delivery catheter apparatus, according to some embodiments of the disclosure.

FIG. 5 is an enlarged side view of the portion of the implantable medical device and delivery catheter apparatus system 54 of FIG. 4 where the implantable medical device 10 couples to the delivery catheter apparatus 32, according to some embodiments of the disclosure. In FIG. 5, the external threads 50 of the driver wedge 38 engage the first set of internal threads 28 of the first prong 16 and the second set of internal threads 30 of the second prong 18 (FIG. 2). So engaged, the driver wedge 38 acts as a wedge, flexing the first prong 16 and the second prong 18, forcing the first prong 16 and the second prong 18 apart from each other into an expanded configuration. Together, the first flange 24 and the second flange 26 extend to a second flange diameter F2 in the expanded configuration.

The first lumen diameter D1 is greater than the first flange diameter F1 (FIG. 1) and less than the second flange diameter F1. The second lumen diameter is greater than equal to the second flange diameter F2. The third lumen diameter D3 is less than the second flange diameter F2. Thus, the second flange diameter F2 is sized such that the first flange 24 and the second flange 26 extend into the annular recess 44 of the delivery catheter 34. So configured, the implantable medical device 10 is coupled to the delivery catheter apparatus 32 because the second flange diameter F2 is greater than the first lumen diameter D1 and the third lumen diameter D3, trapping the first flange 24 and the second flange 26 within the annular recess 44.

Figure 6:
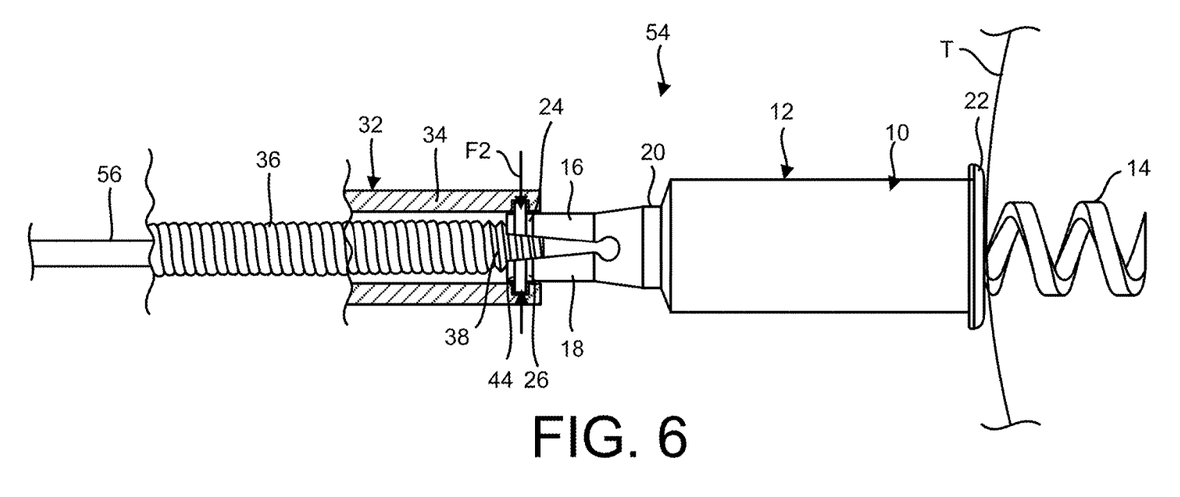
FIG. 6 is a side view of the implantable medical device and delivery catheter apparatus system of FIG. 4 with a fixation device deployed to implant the implantable medical device, according to some embodiments of the disclosure.

FIG. 6 is a side view of the implantable medical device and delivery catheter apparatus system 54 of FIG. 4 with the fixation device 14 deployed to implant the implantable medical device 10, according to some embodiments of the disclosure. The implantable medical device 10 is coupled to the delivery catheter apparatus 32 with the first prong 16 and the second prong 18 in the expanded configuration with the first flange 24 and the second flange 26 engaging the annular recess 44, as shown in FIG. 5. In the embodiment shown in FIG. 6, the delivery catheter apparatus 32 further includes a stylet 56. The stylet 56 is configured to extend through the driver coil lumen 48 and the driver wedge lumen 52 (FIG. 3) and within the device housing 12 along the longitudinal axis A (FIG. 1) to engage the fixation device 14. A distal tip (not shown) of the stylet 56 has a shape configured to engage the fixation the fixation device 14, such as hexagonal, flat blade, cross-shaped, or a multi-point star-shaped pattern, for example. Once the implantable medical device 10 is in a location suitable for fixation and pressed against tissue T, the stylet 56 is rotated to extend the fixation device 14 out of the distal end 22 of the device housing 12 and into the tissue T to implant the implantable medical device 10, as shown in FIG. 6. Once the implantable medical device 10 is implanted, the stylet 56 can be withdrawn from the catheter lumen 42 (FIG. 3).

In some other embodiments, the fixation device 14 may be driven in to the tissue T by other mechanisms, such as by rotating the delivery catheter 34, and/or the driver coil 36, for example.

Figure 7:
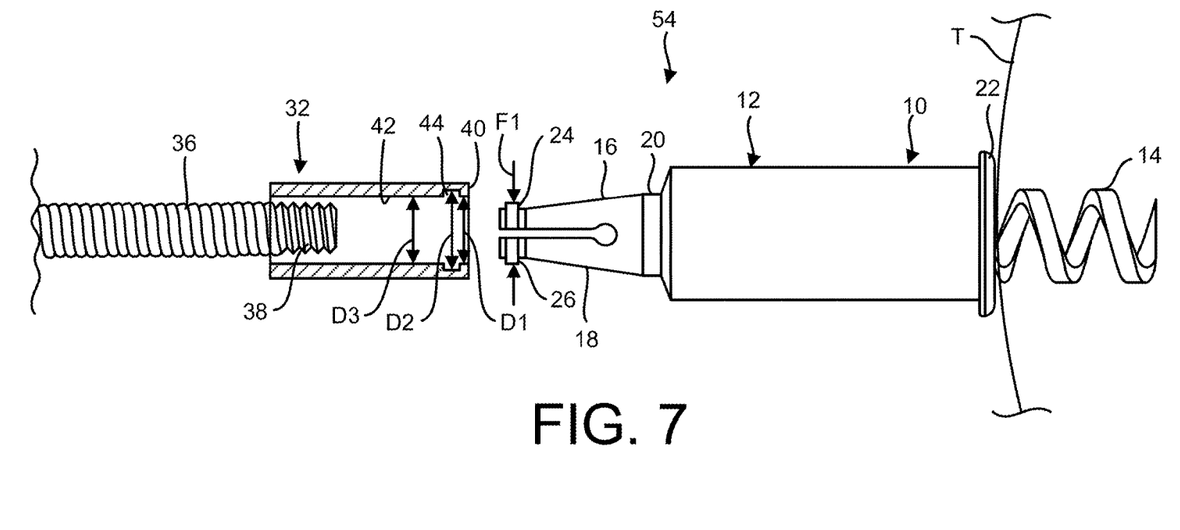
FIG. 7 is the side view of the embodiment of FIG. 6, illustrating decoupling of the delivery catheter apparatus from the implantable medical device, according to some embodiments of the disclosure.

FIG. 7 is the side view of the embodiment of FIG. 6, illustrating decoupling of the delivery catheter apparatus 32 from the implantable medical device 10, according to some embodiments of the disclosure. In FIG. 7, the driver wedge 38 is rotated to disengage the driver wedge 38 from the first prong 16 and the second prong 18. Specifically, as the driver wedge 38 is rotated, the external threads 50 disengage the internal threads 28 of the first prong 16 and the internal threads 30 of the second prong 18. In the embodiment shown in FIG. 7, the driver wedge 38 is rotated by rotating the driver coil 36. In some other embodiments, the driver wedge 38 may be rotated by a stylet similar to the stylet 56, but configured to engage the driver wedge 38.

Once the driver wedge 38 is disengaged from the first prong 16 and the second prong 18, the driver wedge 38 is removed from between the first prong 16 and the second prong 18, releasing a compressive force exerted by the first prong 16 and the second prong 18 on the driver wedge 38. The released compressive force moves the first prong 16 and the second prong 18 toward each other to the relaxed configuration. In the relaxed configuration, the first flange 24 and the second flange 26 extend to the first flange diameter F1. The first flange diameter F1 is less than the first lumen diameter D1. Thus, in the relaxed configuration, the first flange 24 and the second flange 26 are not disposed within the annular recess 44. As the delivery catheter apparatus 32 is retracted proximally, the first flange 24 and the second flange 26 pass out of the catheter lumen 42 through the first lumen diameter D1 to uncouple the delivery catheter apparatus 32 from the implanted implantable medical device 10, as shown in FIG. 7.

Figure 8:
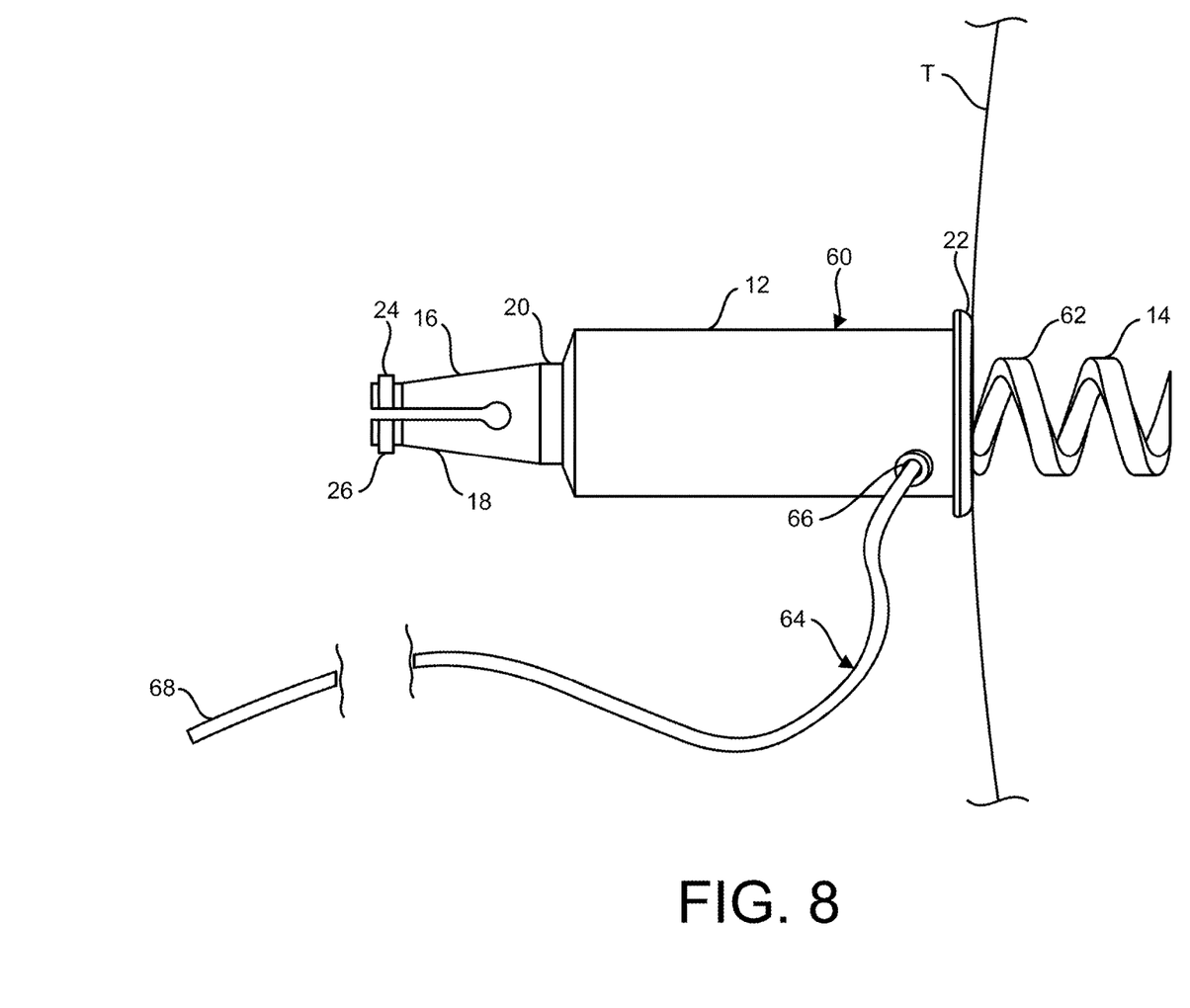
FIG. 8 is a side view of another implantable medical device implanted in the tissue of a patient, according to some embodiments of the disclosure.

FIG. 8 is a side view of an implantable medical device 60 implanted in the tissue T of a patient, according to some embodiments of the disclosure. The implantable medical device 60 is substantially similar to the implantable medical device 10 described above in reference to FIGS. 1, 2 and 4-7, except that it is specifically configured as a medical electrical lead. Thus, the implantable medical device 60 includes an electrode 62 and a conductor 64. In some embodiments, the electrode 62 can be the fixation device 14, such as the fixation helix shown in FIG. 8. In some other embodiments, the electrode 62 can be a conductive band or coil disposed about the device housing 12. In some other embodiments, the electrode 62 can be a conductive ring or plate disposed the distal end 22 of the device housing 12. Although the embodiment of FIG. 8 is shown with a single electrode 62, it is understood that embodiments may include more than one electrode 62 including any of the described electrodes in any combination.

The conductor 64 includes a distal end 66 and a proximal end 68 opposite the distal end 66. The distal end 66 is electrically coupled to the electrode 62. The proximal end 68 is configured to electrically couple to a medical electrical device (not shown) by means know in the art, such as a lead terminal or an electrical feed-thru, for example. The conductor 64 may exit the device housing 12 at the proximal end 20, or along the side of the device housing 12 between the proximal end 20 and the distal end 22, as shown in FIG. 8.

Advantageously, the conductor 64 can have a smaller diameter than typical electrical leads because it does not serve as a portion of the delivery catheter apparatus 32 or to activate the fixation device 14. In some embodiments, a diameter of the conductor 64 can be as small as 0.1 mm, 0.2 mm, 0.3 mm, 0.4 mm, 0.5 mm or 0.6 mm, or as large as 0.7 mm, 0.8 mm, 0.9 mm, 1.0 mm, 1.1 mm or 1.2 mm, or may be within any range defined between any two of the foregoing values, such as 0.1 mm to 1.2 mm, 0.2 mm to 1.1 mm, 0.3 mm to 1.0 mm, 0.4 mm to 0.9 mm, 0.5 mm to 0.8 mm, 0.6 mm to 0.7 mm, 0.3 mm to 0.7 mm, 0.2 mm to 0.6 mm, or 0.7 mm to 1.1 mm, for example.

In some embodiments, the conductor 64 can consist of a single insulated wire. In other embodiments, the conductor 64 can include multiple wires in straight or twisted arrangements. In some other embodiments, the conductor 64 can include a coiled conductor, such as U.S. Pat. No. 9,199,077, entitled "MRI conditionally safe lead with multi-layer conductor".

In use, therapy may be provided from the medical electrical device to the tissue T by way of the conductor 64 and the electrode 62. Alternatively, or additionally, electrical measurements of the activity around the tissue T may be provided to the medical electrical device by way of the electrode 62 and the conductor 64. The implantable medical device 60 poses significantly less risk of perforation or dislodgement from the tissue T due to the small mass of the implantable medical device 60 and the low stiffness of the conductor 64.

Figure 9:
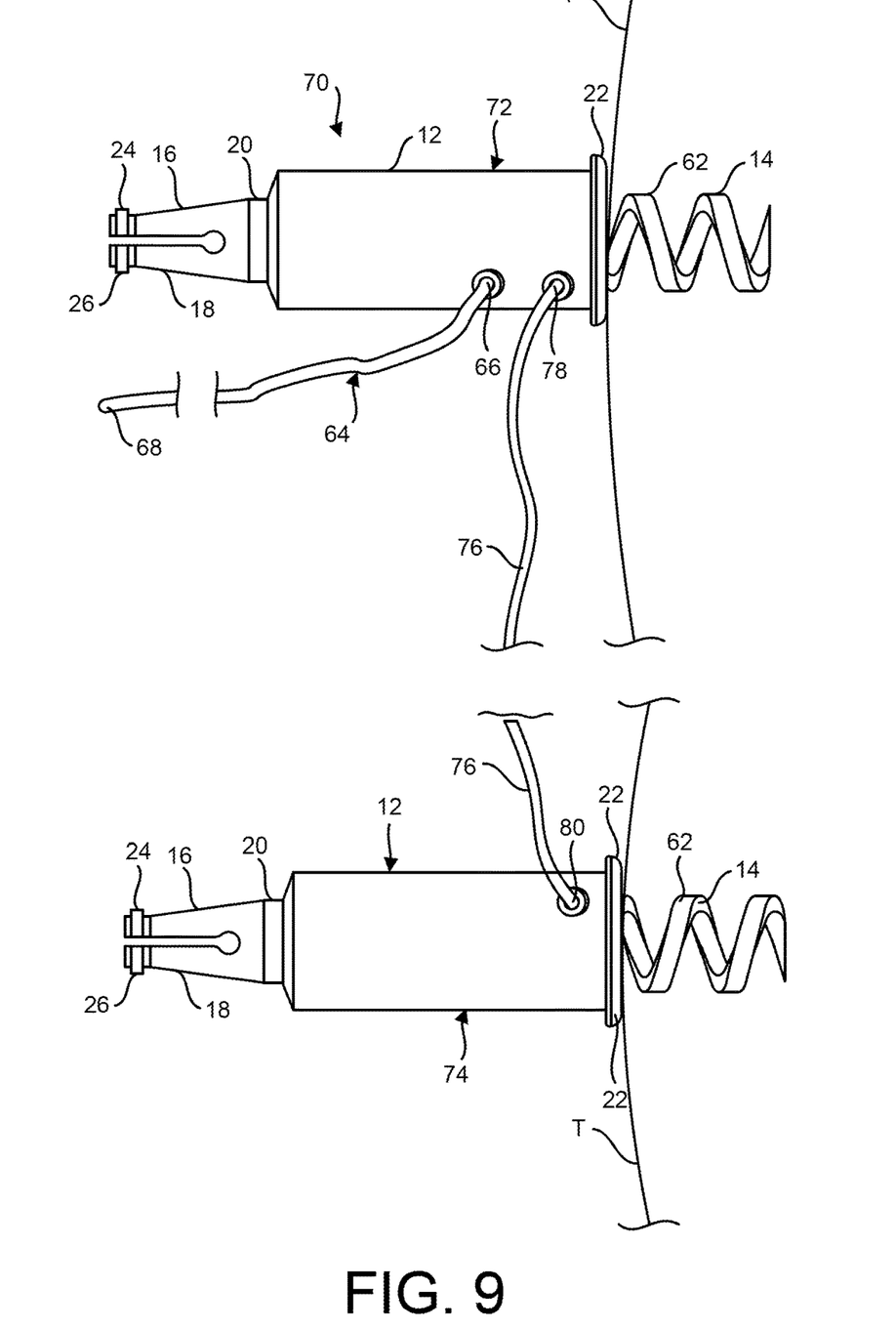
FIG. 9 is a side view of another implantable medical device implanted in the tissue of a patient, according to some embodiments of the disclosure.

FIG. 9 is a side view of an implantable medical device 70 implanted in the tissue T of a patient, according to some embodiments of the disclosure. The implantable medical device 70 includes a first implantable medical device 72 and a second implantable medical device 74. The first implantable medical device 72 is configured as a medical electrical lead and is substantially similar to the implantable medical device 60 described above in reference to FIG. 8, except that it is also electrically coupled to the second implantable medical device 74 by another conductor 76. The conductor 76 may be substantially similar to the conductor 64, as described above. The conductor 76 includes a proximal end 78 and a distal end 80 opposite the proximal end 78. The proximal end 78 of the conductor 76 is electrically coupled to the first implantable medical device 72.

In use, therapy may be provided from the medical electrical device to the tissue T by way of the conductor 64 and the conductor 76. In some embodiments, the electrode 62 of the first implantable medical device 72 may sense an electrical impulse from one area of tissue T and transmit that impulse along the conductor 76 to the second implantable medical device 74, where it is provided to another are of the tissue T by the electrode 62 of the second implantable medical device 74. In this way, the implantable medical device 70 may be used to bridge a damaged portion of a conductor pathway between the two tissue T areas. As with the embodiment of FIG. 8, the small mass of the implantable medical device 70 and the low stiffness of the conductors 64 and 76 pose significantly less risk of perforation or dislodgement from the tissue T.

Figure 10:
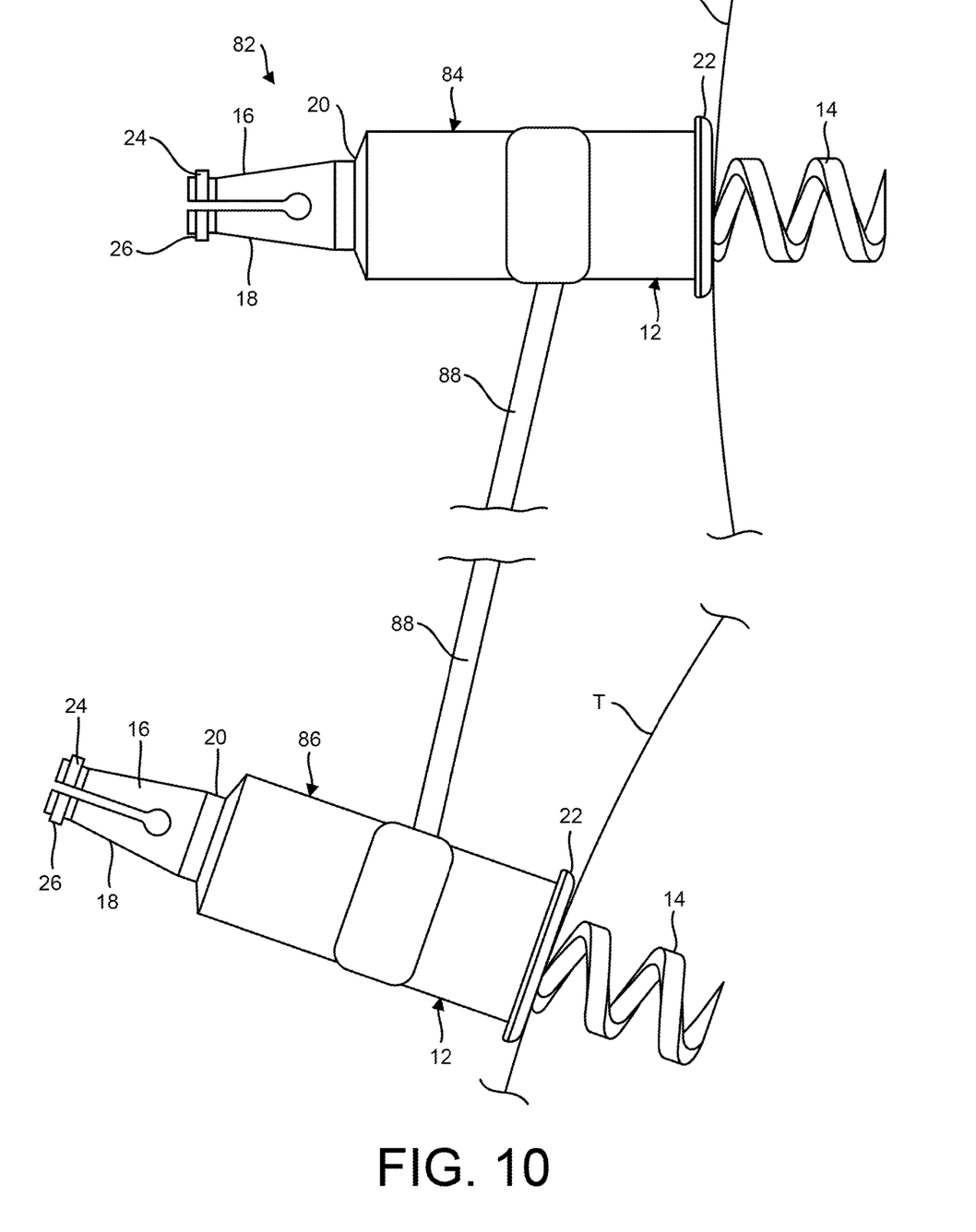
FIG. 10 is a side view of another implantable medical device implanted in the tissue of a patient, according to some embodiments of the disclosure.

FIG. 10 is a side view of an implantable medical device 82 implanted in the tissue T of a patient, according to some embodiments of the disclosure. The implantable medical device 82 includes a first implantable medical device 84, a second implantable medical device 86 and a tether 88. The first implantable medical device 84 and the second implantable medical device 86 are each substantially similar to the implantable medical device 10 described above in reference to FIGS. 1, 2 and 4-7. The first implantable medical device 84 and the second implantable medical device 86 are each tissue anchors. The tether 88 mechanically couples the first implantable medical device 84 and the second implantable medical device 86 together, as shown in FIG. 10.

In use the first implantable medical device 84 and the second implantable medical device 86 may be anchored in portions of the tissue T that need mechanical support to shore up a weakness. The mechanical connection provided by the tether 88 can provide additional mechanical support. As with the embodiments described above, the small mass of the implantable medical device 82 poses significantly less risk of perforation or dislodgement from the tissue T.

Figure 11:
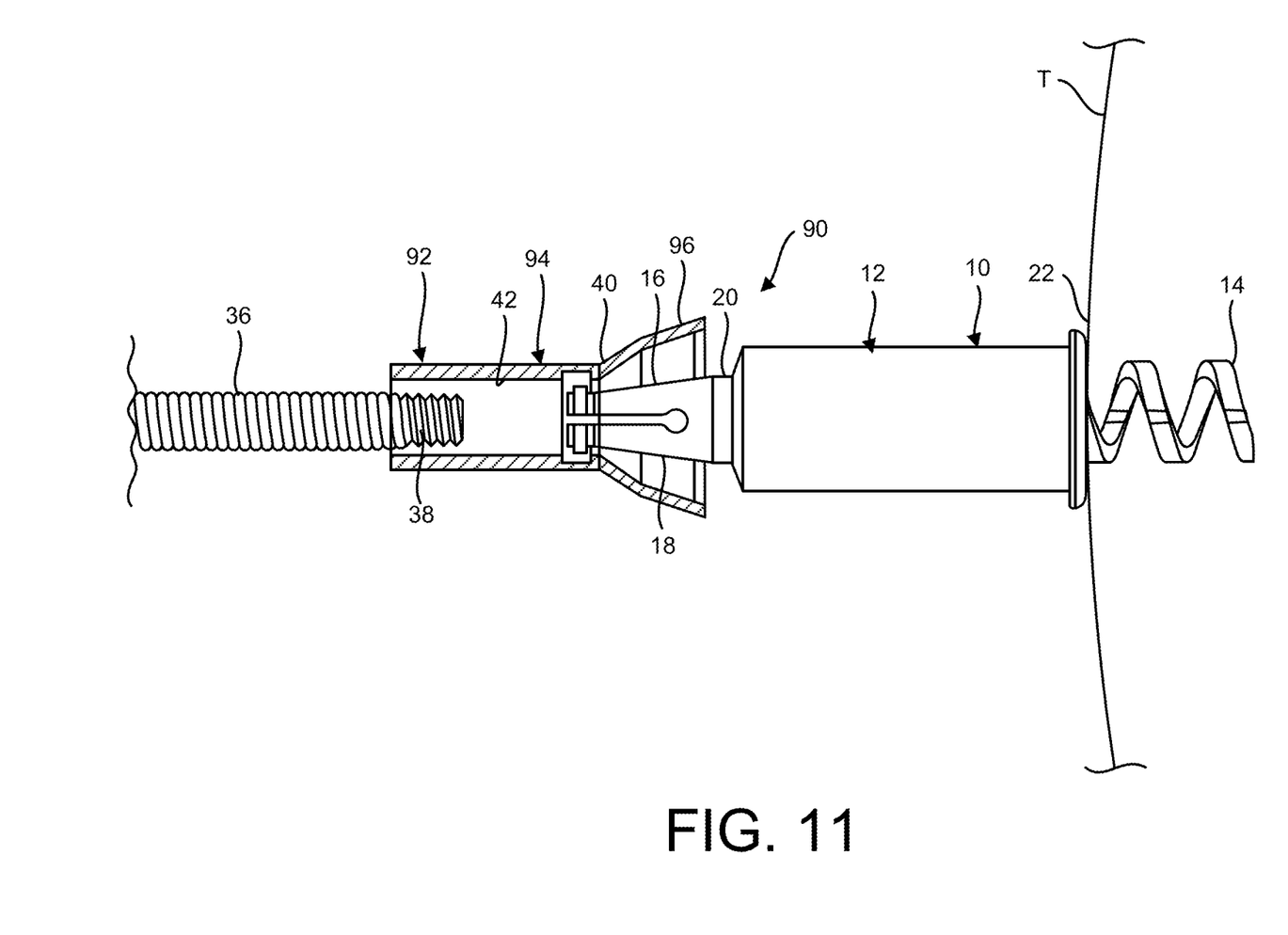
FIG. 11 is a side view of another implantable medical device and delivery catheter apparatus system, according to some embodiments of the disclosure.

FIG. 11 is a side view of an implantable medical device and delivery catheter apparatus system 90, according to some embodiments of the disclosure. The implantable medical device and delivery catheter apparatus system 90 includes the implantable medical device 10, as described above, and with a delivery catheter apparatus 92. The delivery catheter apparatus 92 is substantially similar to the delivery catheter apparatus 32 described above in reference to FIG. 3, except that the delivery catheter 34 is replace by a delivery catheter 94. The delivery catheter 94 is substantially similar to the delivery catheter 34, except that it further includes a cone 96. The cone 96 is a cone-shaped extension of the delivery catheter 34 projecting distally and radially outward from the distal end 40 of the delivery catheter 94. The cone 96 may be formed by flaring an extension of the delivery catheter 94.

Should it become necessary to remove any of the implantable medical devices described above once implanted, such as the implantable medical device 10, the delivery catheter apparatus 92 may be recoupled to the implantable medical device 10, and the fixation device 14 removed from the tissue T by reversing the process described above in reference to FIG. 7. The cone 96 facilitates the recapture of the first prong 16 and the second prong 18, and the re-engagement of the driver wedge 38 with the first prong 16 and the second prong 18.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An implantable medical device comprising:
    a device housing;
    a fixation device configured to extend from a distal end of the device housing;

a first prong projecting from a proximal end of the device housing, the first prong including a first flange projecting away from a longitudinal axis of the device housing; and a second prong projecting from the proximal end of the device housing, the second prong spaced apart from the first prong, the second prong including a second flange projecting away from the longitudinal axis; the first prong and the second prong configured to extend to a first flange diameter in a relaxed configuration and to extend to a second flange diameter in an expanded configuration, wherein the device is configured to couple to a delivery catheter when the first prong and the second prong are in the expanded configuration, and to decouple from the delivery catheter when the first prong and the second prong are in the relaxed configuration.

2. The implantable medical device of claim 1, where in the fixation device is a fixation helix.

3. The implantable medical device of claim 1, further comprising:
an electrode; and
an electrical conductor including a proximal end and a distal end, the distal end electrically coupled to the electrode and the proximal end configured to electrically couple to a medical electrical device.

4. The implantable medical device of claim 3, where in the fixation device is the electrode.

5. The implantable medical device of claim 3, wherein the implantable medical device is a first implantable medical device, further comprising a second implantable medical device substantially similar to the first implantable medical device, the proximal end of the electrical conductor of the second implantable medical device electrically coupled to the first implantable medical device.

6. The implantable medical device of claim 1, wherein the first prong further includes a first set of internal threads projecting toward the longitudinal axis and the second prong further includes a second set of internal threads projecting toward the longitudinal axis, the first set of thread and the second set of internal threads configured to engage the delivery catheter in the expanded configuration and to disengage from the delivery catheter in the relaxed configuration.

7. An implantable medical device and delivery catheter apparatus system comprising:
an implantable medical device comprising:
a device housing;
a fixation device configured to extend from a distal end of the device housing;
a first prong projecting from a proximal end of the device housing, the first prong including a first flange projecting away from a longitudinal axis of the device housing; and
a second prong projecting from the proximal end of the device housing, the second prong spaced apart from the first prong, the second prong including a second flange projecting away from the longitudinal axis; the first prong and the second prong configured to extend to a first flange diameter in a relaxed configuration and to extend to a second flange diameter in an expanded configuration; and
a delivery catheter apparatus including:
a delivery catheter forming a catheter lumen extending from a proximal end of the delivery catheter to a distal end of the delivery catheter;
a driver coil extending through the catheter lumen, the driver coil forming a driver coil lumen; and
a driver wedge disposed at a distal end of the driver coil, the driver wedge configured to selectively engage the first prong and the second prong to place the first prong and the second prong in the expanded configuration, coupling the device to the delivery catheter, and disengage from the first prong and the second prong to allow the first prong and the second prong to return to the relaxed configuration, decoupling the device from the delivery catheter.

8. The system of claim 7, wherein the implantable medical device further includes:
an electrode; and
an electrical conductor, wherein a distal end of the conductor is electrically coupled to the electrode and a proximal end of the conductor is configured to electrically couple to a medical electrical device.

9. The system of claim 8, where in the fixation device is the electrode.

10. The system of claim 8, wherein the implantable medical device is a first implantable medical device and delivery catheter apparatus is a first delivery catheter apparatus, the system further comprising a second implantable medical device substantially similar to the first implantable medical device and a second delivery catheter apparatus substantially similar to the first delivery catheter apparatus, the proximal end of the electrical conductor of the second implantable medical device electrically coupled to the first implantable medical device.

11. The system of claim 7, wherein the catheter lumen includes:
a first lumen diameter at the distal end of the delivery catheter;
a second lumen diameter proximal of the first lumen diameter;
and a third lumen diameter proximal of the second lumen diameter,
wherein the first lumen diameter is greater than the first flange diameter and less than the second flange diameter, the second lumen diameter is greater than or equal to the second flange diameter, and the third lumen diameter is less than the second flange diameter.

12. The system of claim 11, wherein the second lumen diameter forms an annular recess, the first flange and the second flange disposed at least partially within the annular recess in the expanded configuration and not disposed within the annular recess in the relaxed configuration.

13. The system of claim 7, wherein:
the first prong further includes a first set of internal threads projecting toward the longitudinal axis and the second prong further includes a second set of internal threads projecting toward the longitudinal axis; and
the driver wedge further includes a set of external threads configured to selectively engage the first set of internal threads and the second set of internal threads to place the first prong and the second prong in the expanded configuration and to disengage the first set of internal threads and the second set of internal threads to allow the first prong and the second prong to return to the relaxed configuration.

14. The system of claim 7, wherein the driver wedge forms a driver wedge lumen extending through the driver wedge.

15. The system of claim 14, wherein the delivery catheter apparatus further includes a stylet configured to extend through the driver coil lumen and the driver wedge lumen and engage the fixation device to extend the fixation device from the distal end of the device housing.

16. The system of claim 7, wherein the delivery catheter includes a cone projecting distally and radially outward from the distal end of the delivery catheter.

17. A method of decoupling a delivery catheter apparatus from an implantable medical device, the implantable medical device including a first prong including a first flange and a second prong including a second flange, the first flange and the second flange engaging an annular recess in a delivery catheter of the delivery catheter apparatus to couple the implantable medical device to the delivery catheter apparatus, the method comprising:
- rotating a driver wedge to disengage the driver wedge from the first prong and the second prong;
- removing the disengaged driver wedge from between the first prong and the second prong to release a compressive force exerted by the first prong and the second prong on the driver wedge, the released compressive force moving the first prong and the second prong toward each other, disengaging the first flange and the second flange from the annular recess; and
- retracting the delivery catheter proximally to uncouple the delivery catheter apparatus from the implantable medical device.

18. The method of claim 17, wherein rotating the driver wedge includes rotating a driver coil coupled to the driver wedge.

19. The method of claim 17, wherein the implantable medical device is a medical electrical lead.

* * * * *